(12) United States Patent
Gerberich et al.

(10) Patent No.: US 6,444,842 B1
(45) Date of Patent: Sep. 3, 2002

(54) CONTINUOUS PROCESS FOR THE PRODUCTION OF CARBOXYLIC ACID ESTERS OF ALKYLENE GLYCOL MONOALKYL ETHERS

(75) Inventors: H. Robert Gerberich; R. Jay Warner, both of Corpus Christi, TX (US)

(73) Assignee: Celanese International Corporation, Dallas, TX (US)

( * ) Notice: Subject to any disclaimer, the term of this patent is extended or adjusted under 35 U.S.C. 154(b) by 0 days.

(21) Appl. No.: 09/529,899
(22) PCT Filed: Oct. 31, 1997
(86) PCT No.: PCT/US97/19827
§ 371 (c)(1), (2), (4) Date: Apr. 19, 2000
(87) PCT Pub. No.: WO99/23058
PCT Pub. Date: May 14, 1999

(51) Int. Cl.⁷ .......................... C07C 67/02; C07C 67/00; C07C 69/63
(52) U.S. Cl. ....................... 560/264; 560/264; 560/266; 560/239; 560/231; 560/226
(58) Field of Search ................................ 560/264, 266, 560/239, 231, 226, 227, 248

(56) References Cited

U.S. PATENT DOCUMENTS 5,321,152 A * 6/1994 Chu et al.

FOREIGN PATENT DOCUMENTS

EP 0 119 833 B1 3/1984

* cited by examiner

Primary Examiner—Johann Richter
Assistant Examiner—Farhad Forohar
(74) Attorney, Agent, or Firm—M. Susan Spiering

(57) ABSTRACT

The present invention provides an improved method for the preparation of carboxylic acid esters of alkylene glycol monoalkyl ethers by the acid catalyzed esterification of the monoalkyl ether with a carboxylic acid. In a preferred embodiment of the invention, the carboxylic acid and alcohol are reacted in a reactor/column and the resulting ester product is distilled into an overhead decanter/extractor as a single phase. A small amount of solvent, preferably a hydrocarbon is added to the mixture causing the resulting distillate to separate into two phases, one phase containing the desired product, the other containing primarily water. The process described is applicable to both batch and continuous operation and is not constrained by the difficulty of separating closely boiling azeotropes and results in substantially higher production rates than achieved by current processes.

8 Claims, 1 Drawing Sheet

APPARATUS FOR PRODUCING 1-METHOXY-2-PROPYL ACETATE
USING CYCLOHEXANE PHASING AGENT

APPARATUS FOR PRODUCING 1-METHOXY-2-PROPYL ACETATE
USING CYCLOHEXANE PHASING AGENT

CONTINUOUS PROCESS FOR THE PRODUCTION OF CARBOXYLIC ACID ESTERS OF ALKYLENE GLYCOL MONOALKYL ETHERS

CROSS REFERENCE TO RELATED APPLICATION

The present application is based on PCT application: PCT/US 97/19827.

FIELD OF THE INVENTION

The present invention relates generally to preparation of carboxylic acid esters and specifically to a method for preparing alkoxy alkyl esters.

BACKGROUND OF THE INVENTION

The present invention is directed to preparation of carboxylic acid esters and specifically to a method for preparing alkoxy alkyl esters of alkylene glycol monoalkyl ethers in a continuous mode. The reaction liberates water which in addition to unreacted reactants causes operational and purification problems.

In continuous processes to produce esters by reaction of an alcohol and a carboxylic acid, the water of reaction is removed to increase conversion. Typically, the reaction is carried out using a reactor containing a mixture of alcohol, carboxylic acid, ester, water, and an acid catalyst. The reactor is heated to obtain an equilibrium mixture and the products distilled in a fractionating column. As product is distilled alcohol and carboxylic acid are fed to the reactor. With simple esters such as ethyl acetate and butyl acetate the water is removed as azeotropes with the ester and unconverted alcohol. The distillate separates into two liquid phases. The upper phase, referred to as the 'oil phase', contains mainly ester with a little alcohol and some water. The lower phase, referred to as the 'water phase', contains mostly water with some ester and alcohol. The water phase is transferred to a distillation tower and the water discharged from the bottom of the tower as waste; the distillate is recycled. The oil phase is distilled in a purification tower to produce a base discharge product of pure ester and a distillate which is recycled to the reactor. This process has been optimized over the years to allow production of these simple esters at high rates.

When it is attempted to esterify alkylene glycol monoalkyl ethers such as 1-methoxy-2-propanol using this process it has been found to work poorly, if at all. The distillate from the reactor column does not readily separate into two phases, making it very difficult to remove the water of reaction by the above process. The reason that phase separation does not occur is that the alcohol and ester are much more soluble in water compared to simple ester. It has been found that it is possible to operate the reactor/distillation tower in such a manner so as to separate two closely boiling azeotropes (one richer in the alkylene glycol monoalkyl ether and the other richer in the corresponding ester). Although this can be accomplished by operating the distillation tower at a high reflux to distillate ratio, operation of the distillation tower in this manner greatly decreases its capacity. This produces a distillate, which does separate into an oil phase and a water phase, but the degree of separation is poor. Furthermore, the reactor/distillation tower must be operated at such a low rate to make the overall production economically unfeasible.

Because of the solubility problem described above, the alkylene glycol monoalkyl ether esters are usually manufactured by a process described in European Patent Application 0119833 B1. A compound such as toluene is added to the reactor and the water is removed by distillation as an azeotrope with toluene. This drives the reaction to completion. The azeotrope separates into two phases; the water is removed as the water phase and the oil phase is recycled to the reactor. In this process only water is distilled as the azeotrope, leaving ester, unreacted alcohol or carboxylic acid, and catalyst in the reactor. This process requires removal of the catalyst from the product by neutralization or some other means prior to purification. Another drawback is that these processes are normally run in batches rather than in a continuous mode and result in low raw material efficiencies and loss of catalyst. Moreover, ester made this way tends to have problems with acidity and stability.

SUMMARY OF THE INVENTION

It is an object of the present invention to overcome the foregoing difficulties. We have discovered that an alkylene glycol monoalkyl ether ester, such as 1-methoxy-2-propyl acetate can be produced in a continuous process in high yield, at high rate, with excellent product quality, and without catalyst loss. This is accomplished using water as the azeotropic agent and distilling the product as an azeotrope of water, carboxylic acid ester, and some unreacted glycol ether alcohol from the reactor into an overhead decanter/extractor. This product results in a single phase. A small amount of an inert solvent is fed to the decanter/extractor causing the distillate to separate into an oil phase and a water phase. The oil phase contains primarily the solvent, ester, and a small amount of water and reacted alcohol. The water phase contains primarily water and unreacted alcohol and some ester. Unreacted carboxylic acid and catalyst remain in the reactor. This process is not constrained by the difficulty in separating closely boiling azeotropes or higher boiling ester products and results in substantially higher production rates. Moreover, the carboxylic acid is not distilled overhead and does not contaminate the product.

DESCRIPTION OF THE INVENTION

Figure 1:
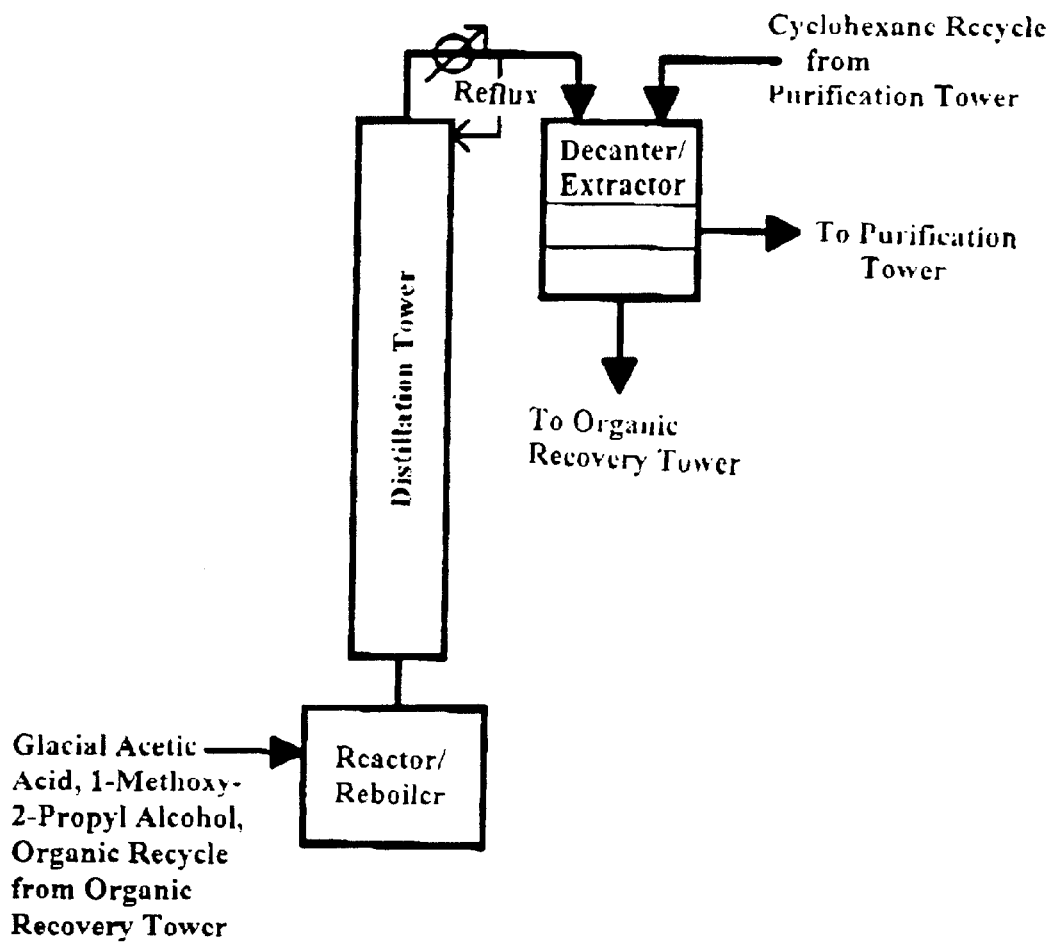
FIG. 1 illustrates a preferred embodiment of the present invention and illustrates the esterification procedure employing a reactor/reboiler, a distillation tower and a decanter/separator.

The present invention provides a method to manufacture alkoxy alkyl esters by the reaction of a carboxylic acid and an alcohol. In a preferred embodiment of the invention, the carboxylic acid and alcohol are reacted in a reactor/reboiler and the resulting ester product is water azeotropically distilled into an overhead decanter/extractor as a single phase. A small amount of an extraction solvent is added to the mixture causing the resulting distillate to separate into two phases, one phase containing the desired product, the other containing primarily water. The process described is not constrained by the difficulty of separating closely boiling azeotropes of reactants and products or by high boiling point ester products, and results in substantially higher production rates than achieved by current processes.

In accordance with this invention there is provided a method for the preparation of carboxylic acid esters of alkylene glycol monoalkyl ethers comprising:

a) reacting a monocarboxylic or halogenated monocarboxylic acid having from 1 to about 10 carbon atoms, with an alkylene glycol monoalkyl ether having the formula

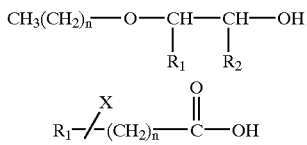

wherein
n=0–6;
$R_1$, $R_2$=H, $CH_3—(CH_2)_n—$; provided when n=6, $R_1$ or $R_2$=H, and
X=Cl, Br, F
in the presence of an acid catalyst; the X group may be located anywhere in the chain;
b) distilling the mixture in a distillation tower, while using water to azeotrope the carboxylic acid ester and unreacted alkylene glycol monoalkyl ether;
c) directing the distillate of (b) to an overhead extractor and contacting with an effective amount of inert solvent (also referred to as phase separating agent) to enable formation of at least two liquid phases;
d) separating the resulting phases of the mixture (water phase and oil product) phase);
e) distilling the oil phase to recover (substantially pure) monocarboxylic acid ester product and inert solvent (for recycle); and,
(f) distilling the water phase (to remove water for waste disposal and alcohol and ester for recycle).

The process can be applied to a continuous or batch reaction set up. It is preferably applied to a continuous reaction setup involving a reactor column, a distillation tower and an overhead decanter/extractor.

Examples of $C_{1-10}$ acids include but are not limited to: acetic acid, formic acid, propionic acid, i-butyric acid, and n-butyric acid. Examples of glycol esters of the product of the process include but are not limited to 1-ethoxy-2-ethyl acetate, 1methoxy-2-propyl acetate, and 1-methoxy-2-propyl propionate. Examples of useful ethers include: 2-ethoxyethanol, and 1-methoxy-2-propanol, and the like.

The reaction is catalyzed by an acid such as a mineral acid such as concentrated sulfuric acid, hydrochloric acid, nitric acid and the like. Lewis acids such as boron trifluoride, antimony pentafluoride and the like may also be employed. Organic sulfonic acids and halogenated sulfonic acids such as methane, ethane and butane sulfonic acids, trifluoromethane sulfonic acid, trichloromethane sulfonic acid, o- or p-toluene sulfonic acid, benzene sulfonic acid and the like as well as strongly acidic sulfonated aromatic ionic exchange resins and perfluoroalkane sulfonic acid resins are also useful. The acid catalysts are generally employed in concentrations of from about 0.01 to about 10 wt %, preferably from about 0.1 to about 2.0 wt %, based on the total reaction mixture, which concentrations may vary with the particular acid employed.

The following paragraph explains the difference between the azeotropic processes currently employed and use of a phase separating agent (extraction agent) in our invention. When a hydrocarbon, for example, is used as an azeotropic agent in a process, it is added to or present in the reactor/reboiler. A constant boiling mixture distills through the distillation tower to produce a distillate containing the hydrocarbon and other components, in this case, primarily water. The desired product, unreacted alcohol and/or carboxylic acid, and catalyst is left in the reactor/reboiler. When a hydrocarbon is used as a phase separating agent (extraction agent) in the process of this invention, it is added to the overhead decanter/separator, causing the product to separate into two phases. By operating this way no carboxylic acid is distilled, greatly simplifying purification of the product.

Useful phase separating agents include those solvents which are inert, have compatible chemistry with the reaction components and cause the desired product to separate into phases. Generally, any solvent having these characteristics and low water solubility is suitable. The solvent may be a linear, branched, aromatic, or cyclic hydrocarbon, an ester, ether, ketone, or fluoro chloro compound. Generally, those compounds have from about 5 to 12 carbon atoms. Example of suitable solvents include, but are not limited to: pentane, cyclopentane, hexane, cyclohexane, toluene, benzene, xylene, olefinic hydrocarbons, butyl acetate, propyl acetate, ethyl acetate, methyl t-butylether, diisopropylether, methyl ethyl ketone, methyl propyl ketone, methyl butyl ketone, and corresponding compounds, fluoro chloro hydrocarbons, chloroform, carbon tetrachloride, methylene chloride, and Freons®). Preferred phase separating solvents are $C_5$–$C_{12}$ hydrocarbons, especially when employed under atmospheric conditions. Hydrocarbons greater than $C_{12}$ are not preferred since generally, if the hydrocarbon has too high a boiling point, the hydrocarbon tends to go to the reactor, not to the distillation tower overhead receiver/decanter. If the hydrocarbon has too low a boiling point, it is not practical to employ under atmospheric conditions. Olefinic hydrocarbons may be employed, but are not preferred due to their tendency to polymerize in the reactor.

The phase separating solvent is employed in an effective amount to enable formation of two liquid phases within the decanter/extractor temperature range of operation. Suitable amounts include from about 5 to about 70 wt %, preferably 10 to about 50 wt %, and, most preferably about 20 to about 40 wt %. Too little phase separating agent will not cause phasing, and too much will require excessive equipment size and energy consumption to process.

The acid catalyzed esterification reaction may be carried out in any suitable reactor, said reactor having means for mixing of reactants, regulating temperature of the reaction, and means for separating the desired ester product from the unreacted components, and water which is generated during reaction. In a preferred embodiment, employed, in addition to that mentioned previously, is a distillation column, a condenser and a phase separator or decanter/extractor for removing the solvent(containing product)-water phases, and a means for returning the solvent and the water to a distillation column A general procedure for carrying out the reaction is to charge the glycol ether, carboxylic acid and acid catalyst into a reaction vessel or reaction column. Heat the mixture and maintain at the desired reaction temperature for an appropriate period of time, and then transferring the distilled product mixture to an overhead phase separator. Contacting the mixture in the phase separator with a phase separating solvent and allowing the phases to separate. The product isolation process then proceeds by separating out the resulting phases of the mixture (water phase and oil (containing product) phase), distilling the phases, and recovering the desired monocarboxylic acid ester of interest.

Referring to FIG. 1, illustrated is a reactor/reboiler wherein reactants are contacted together and mixed throughly employing standard reaction engineering methods. If running in a continuous mode, the feed rate of reactants is adjusted to maintain a suitable residence time at reaction temperature. The mixture is directed to the base of a distillation tower wherein ester product, water, and unreacted reactants are distilled. The distilled product stream containing the desired ester product is then directed to a decanter/separator wherein phase separating agent is added to the mixture. Generally within a short amount of time, typically minutes, after adding the phase separating agent, the mixture results in at least two liquid phases. The oil or product phase is separated from the water phase. The product phase is then distilled to achieve a higher level of purity. The water phase containing mostly water, some ester, and some unreacted alcohol is directed to an organic recovery tower.

General reaction conditions for the inventive esterification include a temperature range in the reactor/column of about 80 to about 160° C., a pressure of about 0.1 to 10 atm and a reactor residence time of about 0.3 to about 5 hrs. The three parameters can be adjusted to optimize the process, and will be different for each ester produced. For reasons of economy, the preferred conditions are operation near 1 atm pressure and with a reactor residence time of about 0.5–2 hrs.

Although the method of the present invention is directed to the production of alkylene glycol monoalkyl ether esters, the procedure is applicable to general esterification reactions. Those of skill in the art will also recognize that the present method is broadly applicable to the preparation of other esters such as propylene glycol monobutyl acetate, dipropylene glycol monoctyl butyrate, ethylene glycol monoethylformate, etc., using the appropriate glycol ether and monocarboxylic acid.

The following examples are intended for illustrative purposes and are not intended to limit the scope of the present invention.

EXAMPLES

Example 1

An apparatus was assembled having a 30 tray, 2" diameter Oldershaw distillation column, a reflux condenser, an overhead receiver (decanter), and a reboiler/reactor. Pumps were used to feed fresh material to the reboiler and cyclohexane to the overhead receiver. To the reboiler/reactor was added 62.8 grams of 1-methoxy-2-propyl acetate, 66.0 grams of 1-methoxy-2-propyl alcohol, 132.1 grams of glacial acetic acid, 67.1 grams of water, and 17.9 grams of methanesulfonic acid catalyst The distillation column was operated at atmospheric pressure at a reflux to distillate ratio of 1.0. Fresh material, having a composition of 44.0 wt % 1-methoxy-2-propyl alcohol, 14.0 wt % glacial acetic acid, and 42.0 wt % water, was fed to the reboiler at a rate of 5.28 grams/min. Cyclohexane was fed to the overhead receiver at a rate of 1.07 grams/min. During operation the temperature in the reboiler remained at 112° C. and the temperature at the top tray of the distillation column at 94° C.; this ensured that little or no cyclohexane was present in the distillation tower or reactor/reboiler. The total product rate from the overhead decanter was 6.36 grams/min, including the cyclohexane feed. The condensed distillate immediately separated into an oil phase containing primarily cyclohexane and 1-methoxy-2-propyl acetate and an aqueous phase containing mostly water with some 1-methoxy-2-propyl alcohol and 1-methoxy-2-propyl acetate. Only the aqueous phase was refluxed to the distillation tower. These operating conditions were maintained for five hours.

The composition of the distillate prior to addition of cyclohexane was determined to be 33.1 wt % 1-methoxy-2-propyl acetate, 21.2 wt % 1-methoxy-2-propyl alcohol, and 45.7 wt % water. It was determined from prior experimentation that under these reaction conditions this mixture will not separate into two phases. After addition of cyclohexane and separation of the phases, the oil phase contained 44.1 wt % cyclohexane, 46.6 wt % 1-methoxy-2-propylacetate, 7.7 wt % 1-methoxy-2-propyl alcohol, and 1.6 wt % water. Phasing was also observed with about 10 wt % of cyclohexane.

Example 2

Following the procedure in Example 1, the distillation column was operated at a reflux to distillate ratio of 0.68. Fresh material, having a composition of 47.7 wt % 1-methoxy-2-propyl alcohol, 18.2 wt % glacial acetic acid, and 34.0 wt % water was fed to the reboiler at a rate of 5.85 grams/min. Cyclohexane was fed to the overhead receiver at a rate of 2.01 grams/min. During operation the temperature of the reboiler remained at ~115° C. and the temperature at the top of the distillation tower at ~93° C. The total product rate from the overhead receiver was 7.78 grams/min including the cyclohexane feed. This separated into an oil phase and an aqueous phase as in the previous example. These operating conditions were maintained for five hours.

The composition of the distillate prior to addition of cyclohexane to the overhead receiver was 32.5 wt % 1-methoxy-2-propyl acetate, 19.3 wt % 1-methoxy-2-propyl alcohol, and 48.2 wt % water. It was determined from prior experimentation that this mixture will not separate into two phases.

Composition of product phase after addition of cyclohexane and separation of the phases contained 50.8 wt % cyclohexane, 43.5 wt % 1-methoxy-2-propyl acetate, 5.7 wt % 1-methoxy-2-propyl alcohol, and 0.0 wt % water.

Comparative Example

Many experiments without addition of cyclohexane showed that phase separation could not be achieved in the overhead receiver unless the reflux to distillate ratio in the tower was at least 3.0, and preferably greater than 5.0 using a 30 tray column. At these operating conditions, however, the feed to the reboiler could only be sustained at a rate of ~1.0 g/min. In a practical sense, not even this rate would be possible when recycle of unreacted 1-methoxy-2-propyl alcohol and operation of the water removal column is considered.

The examples show that the desired ester product can be removed at a rate >5 times that when not using a phasing agent. They also show that a distillable product is obtained containing the desired ester, that is free of carboxylic acid reactant. They illustrate a practical process that does not require neutralization of acid catalyst to recover pure product.

What is claimed is:

1. A method for the preparation of a carboxylic acid ester of an alkylene glycol monoalkyl ether comprising a) reacting in a reaction column a monocarboxylic or halogenated monocarboxylic acid having from 1 to 10 carbon atoms with an alkylene glycol monoalkyl ether having the formula

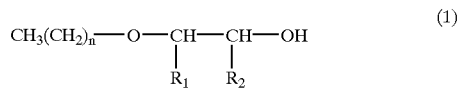

(1)

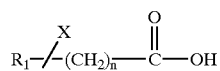

wherein
n=0–6;
$R_1$, $R_2$=H, $CH_3$—$(CH_2)_n$—; provided when n=6, $R_1$ or $R_2$=H, and
X=Cl, Br, F in the presence of an acid catalyst;

b) distilling the mixture in a distillation column, while using the water of reaction to azeotrope the carboxylic acid ester and unreacted alkylene glycol monoalkyl ether;

c) transferring the distillate of (b) to an overhead phase extractor/separator and contacting with an effective amount of inert solvent to enable formation of at least two phases;

d) separating out the resulting phases of the mixture so as to form a water phase and an oil (product) phase; and, e) distilling the oil phase to recover monocarboxylic acid ester product and inert solvent.

2. The method of claim 1 wherein the acid catalyst is selected from the group consisting of concentrated sulfuric acid, hydrochloric acid, nitric acid, boron trifluoride, antimony pentafluoride, methane sulfonic acid, ethane sulfonic acid, butane sulfonic acid, trifluoromethane sulfonic acid, trichloromethane sulfonic acid, o-toluene sulfonic acid, p-toluene sulfonic acid, benzene sulfonic acid, sulfonated aromatic ionic exchange resins and perfluoroalkane sulfonic acid resins.

3. The method of claim 1 wherein the ether is selected from the group consisting of 1-methoxy-2-propanol and 2-ethoxyethanol.

4. The method of claim 1 wherein the inert solvent is linear, branched, aromatic, cycloaromatic hydrocarbon, ester, ether, ketone, and fluoro chloro compounds.

5. The method of claim 4 wherein the solvent is selected from the group consisting of a $C_{5-12}$ hydrocarbon, pentane, cyclopentane, hexane, cyclohexane, toluene, benzene, xylene; and butyl acetate, propyl acetate, ethyl acetate, MTBE, diisopropylethers, methyl ethyl ketone, methyl propyl ketone, methyl butyl ketone, methylene chloride, carbon tetrachloride, and any corresponding branched compounds.

6. The method of claim 5 wherein the solvent is employed at about 5–70 wt %.

7. The method of claim 6 wherein the solvent is employed at about 10–50 wt %.

8. The method of claim 7 wherein the solvent is employed at about 20–40 wt %.

* * * * *